US006902278B2

(12) United States Patent
Bala (10) Patent No.: US 6,902,278 B2
(45) Date of Patent: Jun. 7, 2005

(54) SURGICAL MICROSCOPE DRAPE ASSEMBLY

(76) Inventor: Andrew J. Bala, 48 Golf Ave., Clarendon Hills, IL (US) 60514

( * ) Notice: Subject to any disclaimer, the term of this patent is extended or adjusted under 35 U.S.C. 154(b) by 89 days.

(21) Appl. No.: 10/395,757

(22) Filed: Mar. 24, 2003

(65) Prior Publication Data
US 2004/0190140 A1 Sep. 30, 2004

(51) Int. Cl.[7] .............................................. G02B 11/04
(52) U.S. Cl. ........................ 359/510; 359/511; 359/507
(58) Field of Search ........................ 359/510–511, 507, 359/606; 206/316.1; 600/121–122

(56) References Cited

U.S. PATENT DOCUMENTS

| 3,528,720 A | 9/1970 | Treace .......................... 350/61 |
| 4,183,613 A | 1/1980 | Walchle et al. ............... 350/65 |
| 4,266,663 A | 5/1981 | Geraci ......................... 206/223 |
| 4,561,540 A | 12/1985 | Hunter et al. ............... 206/305 |
| 4,799,779 A | 1/1989 | Mesmer ....................... 350/585 |
| 5,052,789 A | 10/1991 | Kleinberg ................... 359/375 |
| 5,301,657 A | 4/1994 | Lafferty et al. ................. 128/6 |
| 5,311,358 A | 5/1994 | Pederson et al. ........... 359/510 |
| 5,608,574 A | 3/1997 | Heinrich ..................... 359/510 |

(Continued)

FOREIGN PATENT DOCUMENTS

WO      WO 98/50826     11/1998

OTHER PUBLICATIONS

Brochure—*Optics One™ Surgical Microscope Draping System*, "A New Standard in Precise Optics for Microscope Drape", by MTI—Medical Technique, Inc., Tuscon, Arizona (4 pages—undated).

Catalog—*Hospital Products Catalog& Pricelist*—Advanced Medical Designs, Inc., Marietta, Georgia, (28 pages) (undated).

Brochure—*The Science. The Surgeon. One, with Zeiss*, "Opmi Drapes," Carl Zeiss, Surgical Products Division, Thornwood, New York (4 pgs.) Feb., 1996.

Brochure—"Products—Microscope and Equipment Covers" by MTI—Medical Technique, Inc., Tuscon, Arizona (4 pages—undated).

*Primary Examiner*—Mohammad Sikder
(74) *Attorney, Agent, or Firm*—Olson & Hierl, Ltd.

(57) ABSTRACT

The present invention relates to a surgical microscope drape assembly for use with surgical microscopes in an operating room or similar sterile environment. In one embodiment of the invention, the drape assembly comprises an elongated hollow enclosure of sheet-form material having a first end defining an access opening and a second end defining a hole and at least 4 ocular pockets. The access opening of the enclosure allows access to the interior of the enclosure to enable the drape assembly to be pulled over the body of a surgical microscope while the at least four ocular pockets each cover a corresponding ocular port of the microscope to enable the drape assembly to be used on a variety of microscope heads. A view portal, preferably located on the enclosure at the hole proximal to the second end, includes a cylindrical frame with a window support adapted to be located within a cavity of the objective lens barrel of a microscope and a flange adapted for attachment to the sheet-form material of the drape assembly about the hole. The window of the view portal is acutely inclined to minimize glare from an the illumination source and may include at least one layer of anti-reflective coating to at least the upper surface of the window. Optimal viewability through the window occurs when the view portal is mounted on the objective lens barrel to have a rotational orientation of the window inclination towards a first or second ocular port of the microscope. A locator is preferably located on the cylindrical frame to rotationally orient the view portal of the drape assembly in relation to the objective lens barrel of the microscope when mounted thereon.

36 Claims, 4 Drawing Sheets

U.S. PATENT DOCUMENTS

| | | | |
|---|---|---|---|
| 5,682,264 A | * 10/1997 | Cleveland et al. | 359/510 |
| 5,876,328 A | * 3/1999 | Fox et al. | 600/122 |
| 5,882,295 A | * 3/1999 | Kope | 600/122 |
| 5,947,894 A | 9/1999 | Chapman et al. | 600/119 |
| 6,024,454 A | 2/2000 | Horan et al. | 359/510 |
| 6,116,741 A | 9/2000 | Paschal | 359/510 |
| 6,257,730 B1 | 7/2001 | Kleinberg et al. | 359/600 |
| 6,375,610 B2 | 4/2002 | Verschuur | 600/122 |

* cited by examiner

SURGICAL MICROSCOPE DRAPE ASSEMBLY

TECHNICAL FIELD OF THE INVENTION

This invention relates to a surgical microscope drape assembly, the assembly providing at least a fourth ocular pocket within the drape to accommodate at least a fourth ocular eyepiece of a microscope and a lens cover that both minimizes the glare of the microscope's light source on the lens cover window and increases the operative field of the surgeon through the placement of the lens cover window within the cavity of the microscope's objective lens barrel.

BACKGROUND OF THE INVENTION

Microscopes are often used in operating rooms during surgical procedures. During many of these procedures, such as spinal and cranial procedures, the surgeon must manipulate exceptionally small blood vessels, nerve bundles, muscles, nerves and other tissue. These procedures require viewing the surgical site through a surgical microscope so that the fine details in the surgical site can be clearly seen by the surgeon. However, during an operation, the area around the surgical site must remain sterile. A surgical field, as present in a typical hospital's operating room, is an environmentally controlled area where the risk of infection from naturally occurring organisms, such as bacteria, is minimized. The environment's sterility is thus controlled by limiting the introduction of infection-causing bacteria and other contaminants by maintaining strict control over the personnel and equipment present in an operating room.

As it is difficult or impossible to sterilize the surgical microscope, it is common practice to cover the microscope with a sterile drape. The drape typically comprises a flexible tube of sheet-form material that covers all of the components of the surgical microscope, to include the ocular ports of the microscope head and the structure that supports the head. The drape also typically includes a transparent window therein for attachment to the objective lens of the microscope. The drape is typically manufactured and packaged in a sterile condition so that when it is unpackaged in the operating room and placed on a microscope, it creates a sterile field around the microscope and its components.

However, various disadvantages have been realized in trying to adapt sterile drapes to surgical microscopes. One disadvantage arises because many hospitals utilize different configurations of microscopes to perform different types of surgical procedures. Microscopes can be configured to include a variety of ocular view ports in a variety of locations, with such configuration depending on the surgical procedure to be performed. The number and location of ocular ports of a given microscope depends on the surgical procedure taking place and the number of surgeons and or assistants present during the procedure. For example, during cranial operations, surgeons typically stand at the head of the patient side-by-side of one another, with a lead surgeon standing next to one or more assisting surgeons. Thus, with the cranial configuration, the microscope may have up to three ocular ports located approximately side-by-side of one another on one side of the microscope.

This ocular port configuration changes for spinal operations, where surgeons typically stand on opposite sides of a given patient, with a lead surgeon and an assisting surgeon standing preferably 180 degrees from one another on opposite sides of a patient, and up to two assisting surgeons standing on either side of the lead surgeon. With the cranial configuration, the microscope may thus have up to three ocular ports located approximately side-by-side of one another on one side of the microscope and a fourth ocular port located on an opposite side of the microscope, preferably 180 degrees from the lead surgeon's ocular port.

To effectively cover the microscope, it is usually necessary to form the microscope drape with one or more ocular pockets to accommodate the microscope's ocular ports. Prior art drapes have up to three ocular pockets to accommodate the ocular ports of a given microscope. Although such drapes have proven sufficient for use with microscopes configured for cranial operations, with the three ocular pockets accommodating the up to three ocular ports located on one side of a microscope, they prove insufficient during cranial operations requiring the use of four ocular ports. Furthermore, the prior art drapes, having up to three ocular pockets located side-by-side of one another, prove insufficient for use during cranial procedures utilizing as few as two ocular ports, with the two ocular ports used during such procedure being located preferably 180 degrees from one another.

For the prior art drapes to accommodate a microscope having two ocular ports configured for a cranial operation (i.e. located preferably 180 degrees from one another), the ocular pockets of the prior art drape, located side-by-side of one another, must be stretched across the head of the microscope to cover the two opposing ports. Such stretching usually causes tension at some portions of the drape, especially at the joint between the main cover portion and the ocular pockets, thus causing the drape material to deform, rip or rupture. Such a rupture compromises the sterile field established by the drape, requiring a replacement of the drape itself.

Furthermore, in positioning the prior art drapes on the microscope to accommodate the opposing ocular ports, a tearing of the drape may occur around the drape's lens cover, which is typically mounted to the objective lens barrel of the microscope, again compromising the sterile field. Although such tearing may be avoided through a rotation of the lens cover about microscope's objective lens barrel, a rotational adjustment of the lens cover about the barrel may interfere with the optical quality of the image received through the objective lens and drape lens cover. Thus there is a need for a microscope drape having a quantity and location of ocular pockets that can readily accommodate the various configurations of microscope ocular ports commonly used during a variety of surgical procedures.

Another disadvantage associated with prior art drapes arises where the lens cover of such drapes is mounted to the objective barrel such that the lens or window of the cover is located below the lower end of the barrel itself. Such drape lens covers thus result in an increased working distance (depth) of the microscope head during surgical procedures. This increased depth of the microscope results in longer working distances for the surgeon, thus requiring the surgeon to extend his or her arms during surgical procedures performed while viewing the surgical site through the microscope. An increased extension of the arms of the surgeon thus results in the surgeon having reduced surgical control, increased arm and hand fatigue, and decreased hand and finger dexterity.

The location of the drape window below the objective lens barrel also results in the window being located towards the surgical site, thus increasing the likelihood of the occurrence of view obstructions on the window due to blood or tissue particles contacting the window itself. During a given surgical procedure, the microscope head may be repositioned many times in relation to the surgical site. Thus, a window location below the objective lens barrel increases the possibility of the surgeon contacting the window with his or her hands, with such contact again resulting in viewing obstructions occurring on the window. Thus, there is a need for a microscope drape having a lens cover with a window location that results in a reduced working distance (depth) of the microscope head during surgical procedures and a minimization of the occurrence of view obstructions on the window, due to blood or tissue particles contacting the window itself or due to an inadvertent touching of the window by medical staff.

Undesirable complications may also arise where the placement of the drape window below the lens barrel interferes with the surgical procedure itself. For example, the distal end of a surgeon's hand-held instruments may contact or collide with the window during use, thus resulting again in viewing obstructions occurring on the window. Such a collision of the instrument with the window may also interfere with the surgical procedure itself, thus slowing the procedure or adversely affecting the interaction between the instrument and the tissue contacted thereby within the surgical site. Thus, there is a need for a microscope drape having a lens cover with a window location that results in a reduced working distance (depth) of the microscope head during surgical procedures and a minimization of the occurrence surgical interference in the form of collisions between the window of the drape and the hand-held instruments of the surgeon.

In many surgical microscopes, the objective lens transmits light from a light source to the surgical site to illuminate the surgical site, with the objective lens also transmitting the image of the surgical site to the optical path of the microscope. Another disadvantage associated with prior art drapes thus arises where the lens cover results in a degraded optical quality of the viewed image due to a reflection of light from the microscope's light source off of the window of the drape lens and towards the objective lens of the microscope, resulting in glare. In an attempt to remedy this undesirable light reflection and glare, prior art drapes have utilized convex, concave or otherwise curved lens covers or windows to direct the light reflection away from the objective lens.

However, such lenses may cause a distortion of the view of the operative field, resulting in some surgeons discarding the lens or window of the drape lens cover during a given surgical procedure, thus compromising the sterile field around the microscope. With the drape window removed, bacteria or other contaminants present on the objective lens of the microscope itself may fall into the surgical site, thus increasing a likelihood for the occurrence of infection. A removal of the drape window also causes the objective lens of the surgical microscope itself to become exposed to blood and other fluids so that frequent cleaning may be required, thus increasing the potential to scratch or damage the objective lens, an expensive component of the surgical microscope. Finally, a curved drape lens or window results in an undesirable diffraction of a laser beam projected through the lens during image-guided surgeries. Thus, there is a need for an objective lens cover that maintains true sterility within the surgical field and minimizes the occurrence of glare, image distortion and laser diffraction during operative procedures.

Accordingly, there remains a need for a true, sterile surgical microscope drape that can readily accommodate the various configurations of microscope ocular ports commonly used during a variety of surgical procedures, that results in a reduced working distance (depth) of the microscope head during surgical procedures to enable a minimization of the occurrence of view obstructions and surgical interference, and that minimizes glare, image distortion and laser diffraction during operative procedures. The present invention satisfies these needs.

SUMMARY OF THE INVENTION

The present invention generally relates to a drape assembly for use with surgical microscopes. An exemplary surgical microscope may include at least first and second ocular ports, an objective lens barrel, and an illumination source (not illustrated) for illuminating the operative field viewed through the microscope. In one embodiment of the invention, the drape assembly comprises an elongated hollow enclosure of sheet-form material having a first end defining an access opening and a second end defining a hole and at least 4 ocular pockets. In the preferred embodiment of the invention, the sheet-form material is a transparent, flexible material made of polyethylene, polypropylene, or some other similar polymer or copolymer film of a predetermined thickness.

The access opening of the enclosure allows access to the interior of the enclosure to enable the drape assembly to be pulled over the body of a surgical microscope. The access opening is thus pulled over and past the head of the microscope to a location on the microscope away from the head and operative field. The at least four ocular pockets defined in the second end of the enclosure each cover a corresponding ocular port of the microscope when the drape assembly is pulled over the microscope as described above. The at least four ocular pockets enable the drape assembly to be used on a variety of microscope heads having a variety of ocular ports placed in a variety of locations, with the number and location of ocular ports of a given microscope depending on the surgical procedure taking place and the number of surgeons and or assistants present during the procedure.

A view portal is preferably located at the hole on the enclosure proximal to the second end. The view portal includes a cylindrical frame, defining a central axis, and an outer surface engageable with an inner peripheral wall of the objective lens barrel for mounting the frame on the barrel. The cylindrical frame includes a window attached to a window support located at a first end of the frame, with the window support adapted to be located within a cavity of the objective lens barrel when the outer surface of the cylindrical frame engages the inner peripheral wall. A flange, located proximal to a second end of the cylindrical frame and extending outwardly from the frame's outer surface, is adapted for attachment to the sheet-form material of the drape assembly about the hole the enclosure to form a hermetically sealed connection between the two.

The window, located on the window support, is thus located within the cavity of the objective lens barrel when the outer surface of the frame engages the inner peripheral wall of barrel. The location of the window within the cavity is advantageous because it results in a reduced working distance (depth) of the microscope head during surgical procedures and a minimization of surgical interference and of viewing obstructions from occurring on the window itself. The window of the view portal intersects a pair of viewing axes defined by the ocular ports of the microscope and an illumination axis defined by an illumination source within the microscope when the frame is mounted on the barrel.

The window of the view portal is flat and acutely inclined to minimize glare from the illumination source, with the window defining a plane acutely inclined in relation to the central axis of the frame or in relation to the illumination axis of the microscope and the upper surface of the window receiving the illumination axis from the illumination source. In another embodiment of the invention, the anti-glare properties of the inclined window are enhanced through the addition of at least one layer of anti-reflective coating to at least the upper surface of the window receiving the illumination axis from the illumination source.

Optimal viewability through the window occurs when the view axes fall on a common elevation of the inclined window, with the view portal mounted on the objective lens barrel to have a rotational orientation of the window inclination preferably towards the first ocular port or second ocular port of the microscope to ensure such optimal viewability. A locator is preferably located on the cylindrical frame to rotationally orient the view portal of the drape assembly in relation to the objective lens barrel of the microscope when mounted thereon.

DETAILED DESCRIPTION OF THE INVENTION

Figure 1:
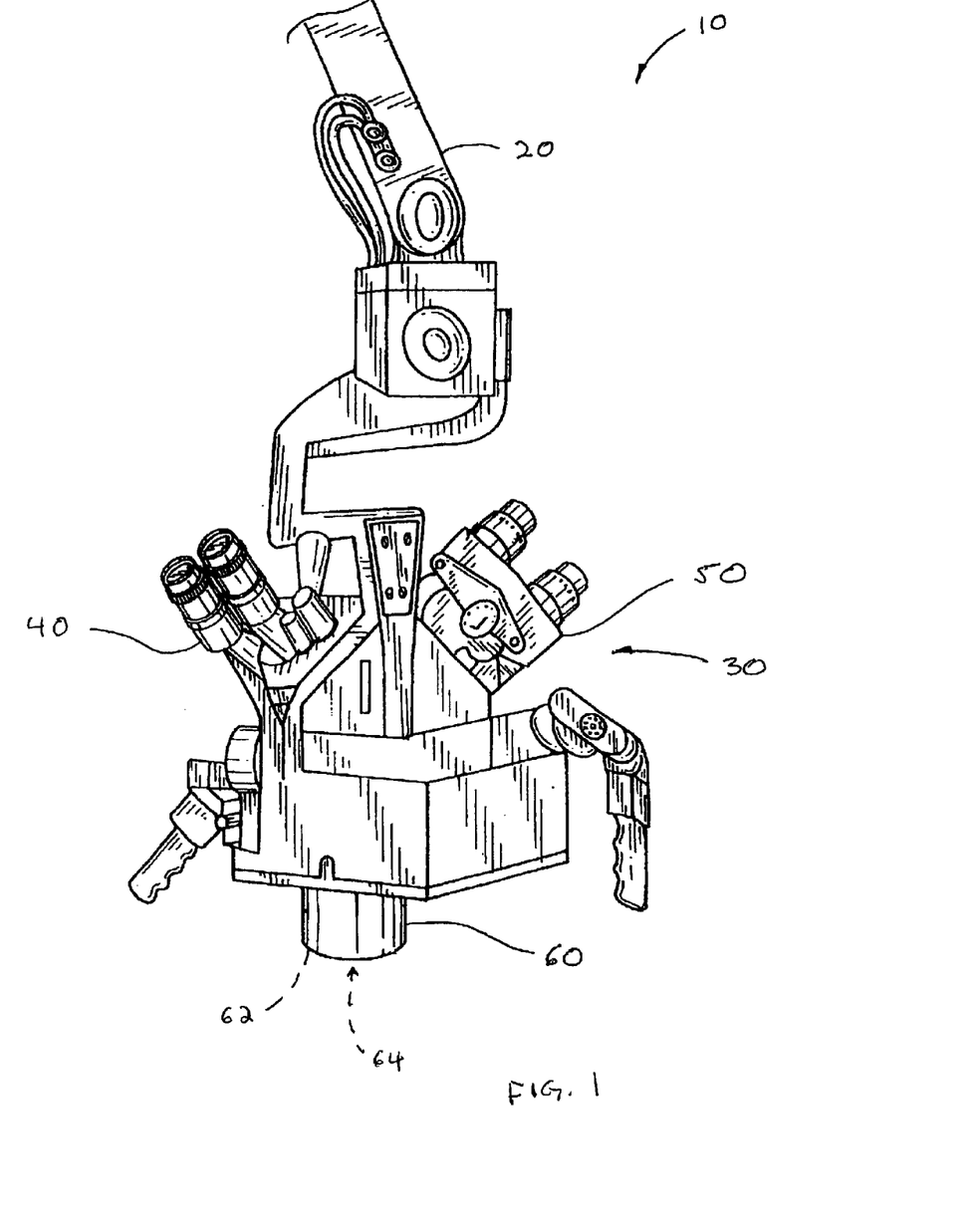
FIG. 1 is a perspective view of an exemplary surgical microscope.

The present invention generally relates to a drape assembly for use with surgical microscopes. FIG. 1 is a perspective view illustrating the basic components of an exemplary surgical microscope 10 to be covered by one embodiment of the drape assembly of FIG. 2. The microscope 10 is adjustably mounted relative to a floor, wall or ceiling mounted structure (not shown) with an articulated support arm 20 supporting a microscope head 30. The microscope head 30, mounted to the free end of the support arm 20, includes at least first and second ocular ports 40 and 50, an objective lens barrel 60, and an illumination source (not illustrated) for illuminating the operative field viewed through the microscope.

Figure 2:
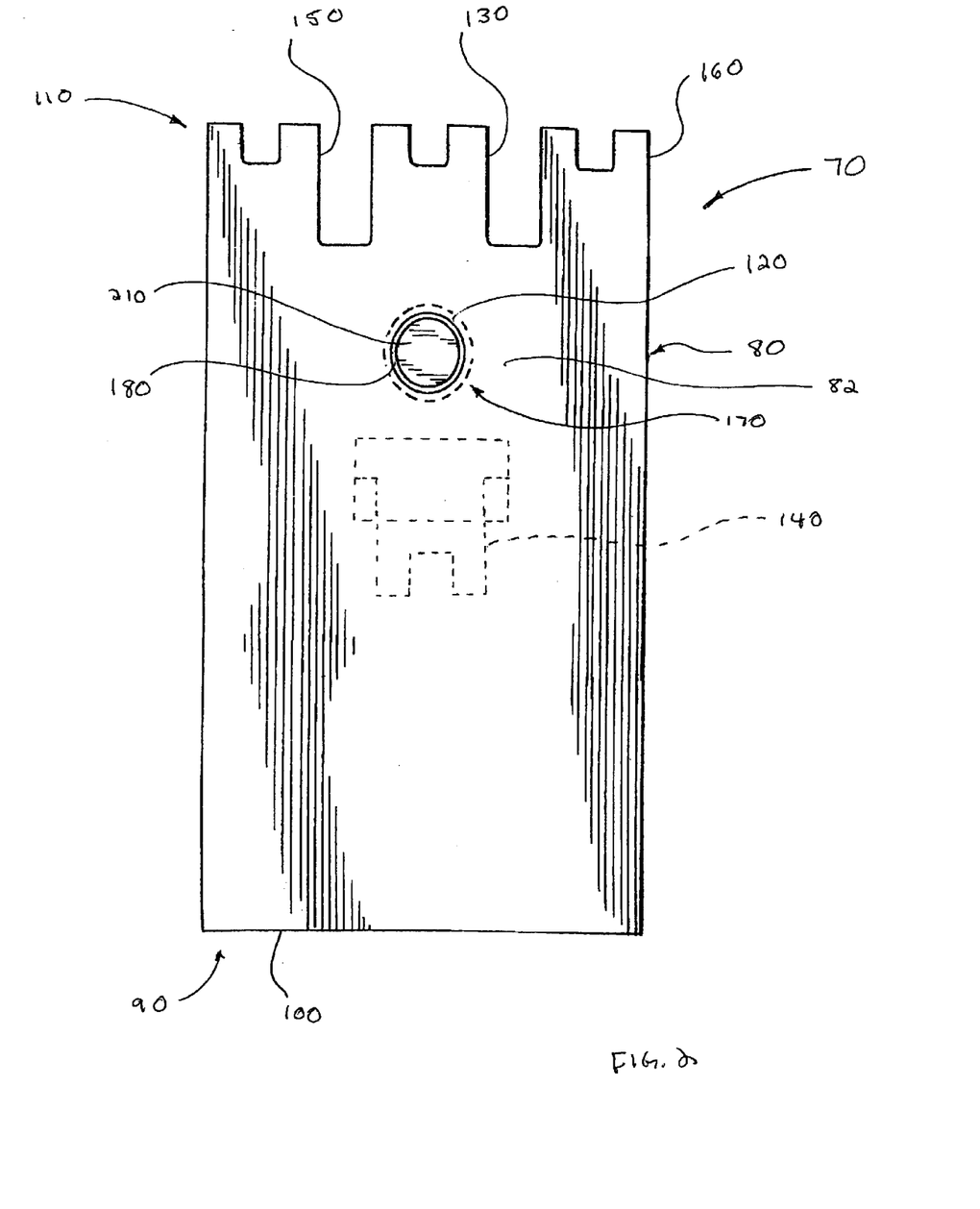
FIG. 2 is a plan view of the drape assembly.
Figure 3:
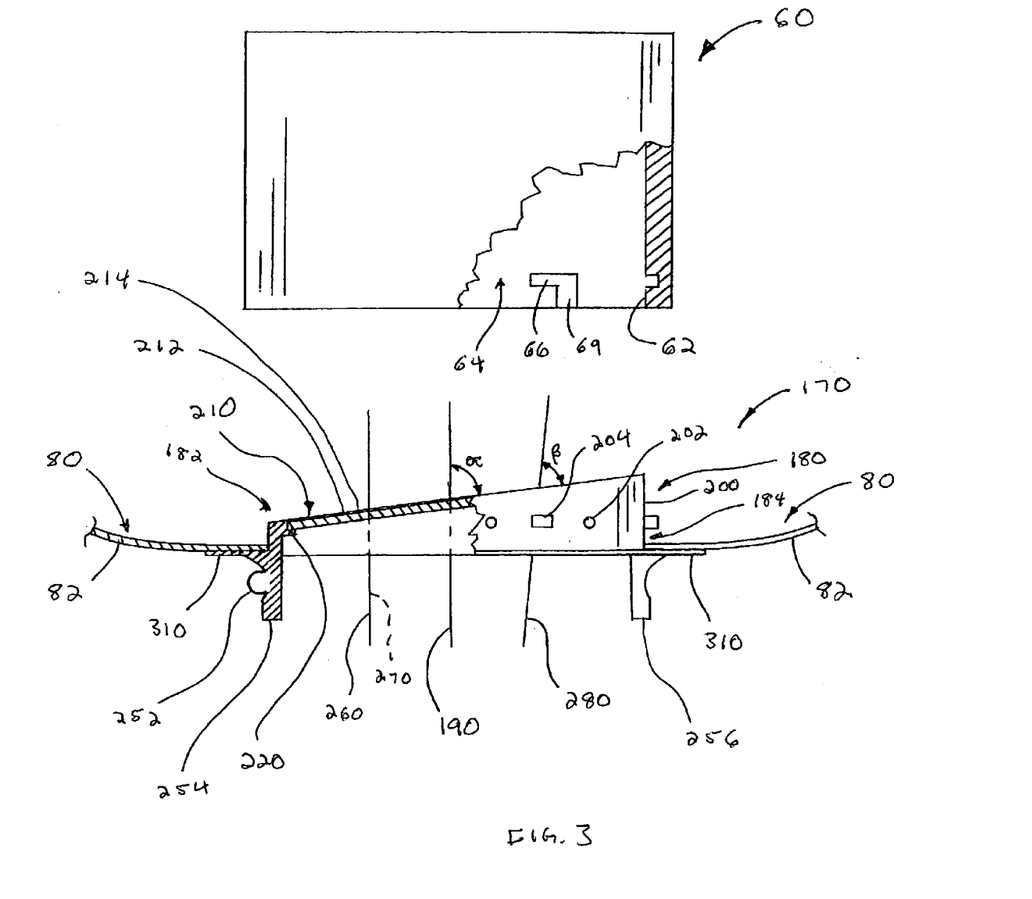
FIG. 3 is a partial sectional elevational view of the objective lens barrel of the microscope and the view portal of the drape assembly.
Figure 4:
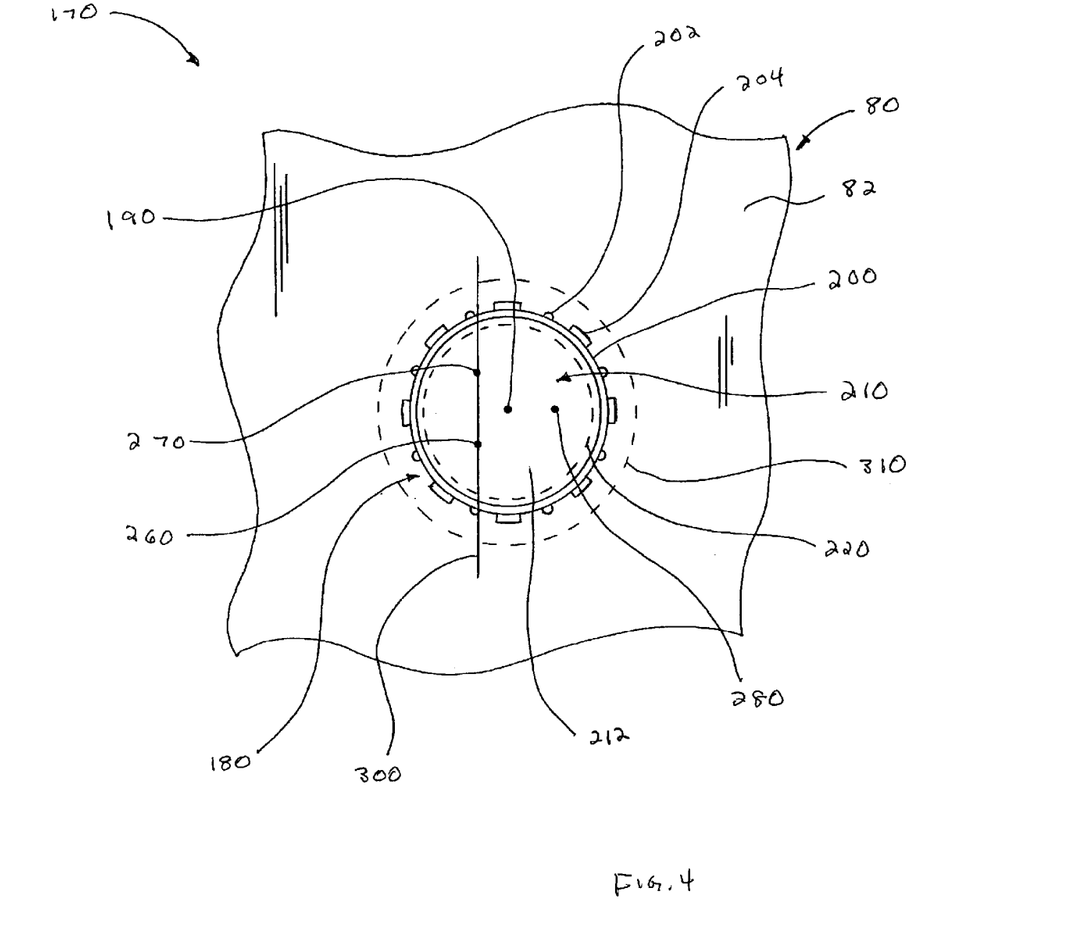
FIG. 4 is a plan view of the view portal of the drape assembly showing an upper surface of the window.

FIG. 2 illustrates one embodiment of the microscope drape assembly 70 that covers the surgical microscope 10 of FIG. 1 while FIGS. 3 and 4 illustrate more detailed views of the view portal of the assembly. In the embodiment shown in FIG. 2, the drape assembly 70 comprises an elongated hollow enclosure 80 of sheet-form material having a first end 90 defining an access opening 100 and a second end 110 defining a hole 120 and at least 4 ocular pockets 130, 140, 150 and 160. A view portal 170 is preferably located at the hole 120 on the enclosure proximal to the second end 110. Referring to FIGS. 3 and 4, the view portal 170 includes a cylindrical frame 180, defining a central axis 190, and an outer surface 200 engageable with an inner peripheral wall 62 of the objective lens barrel 60, for mounting the frame on the barrel.

The cylindrical frame 180 includes a flat window 210 attached to a window support 220 located at a first end 182 of the frame, with the window support adapted to be located within a cavity 64, defined by the inner peripheral wall 62 of the objective lens barrel, when the outer surface 200 of the cylindrical frame 180 engages the inner peripheral wall. The window 210 of the view portal 170 intersects a pair of viewing axes 260 and 270 defined by the ocular ports of the microscope 10 and an illumination axis 280 defined by an illumination source (not shown) within the microscope 10 when the frame 180 is mounted on the barrel 60. The window of the view portal 170 is acutely inclined to minimize glare from the illumination source, with the view portal having a rotational orientation with the lens barrel to enable an optimum viewability through the portal. A locator 250 is preferably located on the cylindrical frame 180 to rotationally orient the view portal 170 of the drape assembly 70 in relation to the objective lens barrel 60 of the microscope 10 when mounted thereon.

Referring again to FIG. 2, the drape assembly 70 has a body that comprises a substantially tubular, elongated hollow enclosure 80 made of a sheet-form material. In the preferred embodiment of the invention, the sheet-form material is a transparent, flexible material made of polyethylene, polypropylene, or some other similar polymer or copolymer film of a predetermined thickness. A first end 90 of the enclosure 80 defines an access opening 100 while a second or opposite end 110 defines at least four ocular pockets 130, 140, 150, 160 and a hole 120.

The access opening 100 of the enclosure 80, defined by the periphery of the tubular enclosure 80 at the first end 90, allows access to the interior of the enclosure 80 to enable the drape assembly 70 to be pulled over the body of a surgical microscope 10. The access opening 100 is thus pulled over and past the head 30 of the microscope (FIG. 1) to a location on the microscope away from the head and operative field (i.e. where the support arm meets the floor, wall or ceiling of the operating room). The at least four ocular pockets 130, 140, 150 and 160, defined in the second end 110 of the enclosure 80, each cover a corresponding ocular port (if present for each pocket) of the microscope 10 when the drape assembly 70 is pulled over the microscope as described above.

The at least four ocular pockets 130, 140, 150 and 160 enable the drape assembly 70 to be used on a variety of microscope heads having a variety of ocular ports placed in a variety of locations. The number and location of ocular ports of a given microscope depends on the surgical procedure taking place and the number of surgeons and or assistants present during the procedure. For example, during cranial operations, surgeons typically stand at the head of the patient side-by-side of one another, with a lead surgeon standing next to an assisting surgeon. With this configuration, the microscope head 30 typically has a first ocular port 40, used by the lead surgeon and centrally located on the microscope head 30 as illustrated in FIG. 1, and a second ocular port (not shown), used by the assisting surgeon and located to the right or left of the first ocular port 40. It is noted that a third ocular port (not shown) may also be utilized during a given cranial procedure, with the third ocular port being located next to the first ocular port 40 on a side opposite the second ocular port. Thus, during cranial operations, up to three ocular ports may be used during a given procedure, with the three ports being located approximately side-by-side of one another on one side of the microscope's head 30.

During spinal operations, however, surgeons typically stand on opposite sides of a given patient, with a lead surgeon standing on one side of the patient and an assisting surgeon standing on the opposite side of the patient, preferably 180 degrees from or facing the lead surgeon. With this configuration, as illustrated in the microscope of FIG. 1, the microscope head 30 typically has a centrally located first ocular port 40 used by the lead surgeon, with a second ocular port 50 used by the assisting surgeon centrally located preferably 180 degrees from the first ocular port. Although the ocular ports of the lead and assistant surgeon are located 180 degrees from one another in the preferred embodiment of the microscope, the location of the ocular ports from one another may be of any angle that enables the surgeons to stand on opposite sides of the patient.

Although not illustrated, an additional assistant or observer may stand on each side of the lead surgeon or assisting surgeon, thus necessitating the use of one or more additional ocular ports, with the one or more additional ocular ports being respectively located on each side of the lead or assistant surgeon's respective first or second ocular port 40 or 50. With this configuration, three ocular ports can thus be located on one side of the microscope head 30 (one on each side of the centrally located first or second ocular ports 40 or 50), with the first and second ocular ports 40 and 50 being located preferably 180 degrees from one another. Thus, during spinal operations, up to four ocular ports may be used during a given procedure, with three ocular ports being located on one side of the microscope head 30 and patient.

The drape assembly of FIG. 2 thus includes at least 4 ocular pockets 130, 140, 150 and 160 to accommodate the microscope configurations requisite of both cranial and spinal operations. For spinal operations utilizing a lead and assisting surgeon and two assistants or observers (three side-by-side ocular ports and one ocular port located preferably 180 degrees of a first port), the drape assembly includes a first centrally located ocular pocket 130 with a second centrally located ocular pocket 140 located preferably 180 degrees from the first pocket. In the embodiment of the invention illustrated in FIG. 2, third and fourth ocular pockets 150 and 160 are located on opposite sides of the first pocket 130. This configuration of ocular pockets thus enables the drape assembly to accommodate a surgical microscope having 4 ocular ports, as described above, with three of the four ocular ports being located on one side of the microscope's head. For cranial operations, however, the first, third and fourth ocular pockets 130, 150 and 160 can accommodate the three ocular view ports located on one side of the microscope head 30. The second ocular pocket 140, located preferably 180 degrees from the first pocket 130, would go un-used during this procedure.

The use of 4 ocular pockets 130, 140, 150 and 160 with the microscope drape assembly thus have the advantage of allowing a single drape assembly to accommodate various surgical procedures, with each procedure having a different ocular port configuration. The use of 4 ocular pockets also has the advantage during spinal procedures of not requiring that the drape assembly enclosure 80 (i.e. an assembly having less than four ocular pockets) be stretched or the view portal 170 be rotated about the objective lens barrel 60 to accommodate the ocular port located 180 degrees from the first port. Such a stretching of the enclosure 80 can compromise the sterile field established by the drape assembly around the microscope, while the rotation of the view portal 170 can compromise the quality of the image received by the objective lens of the microscope.

Located on the enclosure 80 proximal to the ocular ports at the enclosure's second end 110 is hole 120. The hole, having a diameter of predetermined dimension to accommodate the view portal 170 therein, is located preferably on a lower surface 82 of the enclosure 80 to allow the view portal to be mounted on the objective lens barrel 60, located on the lower surface of the microscope head 30. The view portal 170, adapted to be mounted on the objective lens barrel 60 of the microscope, is attached to the sheet-form material of the enclosure 80 about the hole 120 such that the drape assembly 70 is sealed around the view portal 170.

FIGS. 3 and 4 respectively show a side sectional view and plan view of the preferred embodiments of the view portal 170. View portal 170 comprises a cylindrical frame 180 defining first and second ends 182 and 184 and a central axis 190. The cylindrical frame 180 has an outer surface 200 engageable with the inner peripheral wall 62 of the objective lens barrel 60 for mounting the frame on the barrel. In one embodiment of the invention, the outer surface 200 of the frame 180 can include at least one raised resilient surface 202 engageable with the inner peripheral wall 62 of the objective lens barrel 60. In the embodiment shown in FIGS. 3 and 4, the at least one raised resilient surface is comprised of at least one bump or nodule located on the outer surface 200 of the frame 180.

In another embodiment of the invention, the outer surface 200 of the frame 180 can include at least one tab 204 engageable with at least one recess 66 located within the inner peripheral wall 62 of the objective lens barrel 60. With such an arrangement, the at least one tab 204 of the frame 180 is aligned with an at least one recess opening 69, located at the bottom of the inner peripheral wall 62 of the barrel, and the at least one tab is inserted into the opening and the frame 180 raised and rotated until the at least one tab is seated in the at least one recess 66. It is noted that the at least one raised resilient surface 202 and the at least one tab 204 are illustrated in FIGS. 3 and 4 in combination with one another to engage the frame 180 to the inner peripheral wall. However, it is understood that the two can be used in the alternative as well to engage the frame 180 to the inner peripheral wall of the microscope's objective lens barrel 60.

A window support 220 is located proximal to the first end 182 of the cylindrical frame 180 and is adapted to be located within the cavity 64 of the objective lens barrel 60 when the outer surface 200 of the frame engages the inner peripheral wall 62 of the barrel. The window support 220 is preferably a shelf upon which an outer periphery of the window 210 rests when located within the frame 180. The window 210, located on the window support 220, is thus located within the cavity 64 of the objective lens barrel 60 when the outer surface 200 of the frame 180 engages the inner peripheral wall 62 of barrel 60.

The location of the window 210 within the cavity 64 is advantageous because it results in a reduced working distance (depth) of the microscope head during surgical procedures. The reduced depth of the microscope allows for shorter working distances for the surgeon, thus not requiring the surgeon to extend his or her arms during surgical procedures performed while viewing the surgical field through the microscope. A reduced extension of the arms of the surgeon thus enables the surgeon to have better surgical control, less arm and hand fatigue, and improved hand and finger dexterity. The location of the window 210 within the cavity 64 is also advantageous because the window is moved up and away from the surgical field, thus minimizing surgical interference and view obstructions from occurring on the window due to blood or tissue particles contacting the window itself. The location of the window 210 within the cavity 64 also minimizes the possibility of the surgeon contacting the window with his or her hands, with such contact again resulting in viewing obstructions occurring on the window.

Turning again to FIGS. 3 and 4, the window 210 is located on the window support 220 such that the window intersects a pair of viewing axes 260 and 270 and an illumination axis 280 of the microscope, if an illumination source is utilized therein. The pair of viewing axes 260 and 270 are defined by the spaced oculars of each ocular port, thus enabling stereoscopic viewing of the field of operation through each port of the surgical field via the path of the viewing axes through the microscope's objective lens barrel 60 and view portal window 210. The illumination axis 280, if present, is defined by an illumination source (i.e. a xenon light source, not shown), preferably located within the microscope's head 30, that transmits the illumination axis through the microscope's objective lens barrel 60 and through the window 210 of view portal 170, the window having an upper surface 212 receiving the illumination axis from the illumination source to illuminate the field of operation.

Referring to FIG. 3, to minimize any glare that may occur on the objective lens in the viewing axes 260 and 270 due to the reflection of the illumination axis 280 from the window 210 of the view portal 170, in one embodiment of the invention, the window 210 defines a plane acutely inclined in relation to the central axis 190 of the frame 180, with the window defining the plane having an upper surface 212 receiving the illumination axis from the illumination source. In the preferred embodiment of the invention utilizing a window 210 inclination in relation to the frame central axis 190, the angle a of the acute inclination of the window in relation to the frame central axis is from about 81 degrees to about 85 degrees, preferably from about 81 degrees to about 83 degrees, and optimally about 82 degrees.

Alternatively, the window 210 defines a plane acutely inclined in relation to the illumination axis 280 of the microscope, with the upper surface 212 of the window 210 defining the plane receiving the illumination axis from the illumination source. In the preferred embodiment of the invention utilizing a window 210 inclination in relation to the illumination axis 280, the angle β of inclination of the window in relation to the illumination axis is from about 77 degrees to about 83 degrees, preferably from about 77 degrees to about 81 degrees, and optimally about 79 degrees. The angle of the window 210 in relation to the illumination axis 280 takes into account that the illumination axis 280 of the type of microscope shown can have an angle of from about 2 degrees to about 4 degrees in relation to the central axis 190 of the frame 180. The inclination of the window 210, whether in relation to the central axis 190 of the frame 180 or in relation to the illumination axis 280 of the microscope, minimizes any glare or reflection from the illumination axis because any reflection of the illumination axis from the window is deflected away from the viewing axes 260 and 270.

In yet another embodiment of the invention, the anti-glare properties of the inclined window 210 are enhanced through the addition of at least one layer of anti-reflective coating 214 to at least the upper surface 212 of the window receiving the illumination axis 280 from the illumination source. The coating 214 can also be applied to at least the lower surface of the window as well. In the preferred embodiment of the invention utilizing an anti-reflective coating, a coating comprised of about 40% zirconia (ZrO2) and about 60% fluoride (MgF2) is applied by a machine (i.e Optorum Model No. OTFC-1100DB) to the inclined window in about 3 layers to form a coating thickness of about 0.0045 mm.

The zirconia-fluoride coating, having an affinity to absorb red wavelengths of from about 480 nm to about 550 nm, has an index of refraction of about 2.1 on a window having an index of refraction of about 1.6. The coating also has an angle of incidence of from about 0 to about 15, with a reflectance of less than about 2% to yield stray light of less than about 0.8%. When the zirconia-fluoride coating is applied to the upper surface 212 of the window 210 receiving the illumination axis 280 from the illumination source, the inclined window, having an index of refraction of about 1.6, and the zirconia-fluoride coating, having an index of refraction of about 2.1, will have an enhanced minimization of the occurrence of glare.

Because the ocular ports define a pair of illumination axes 260 and 270 to enable a stereoscopic view of the operative field, optimal viewability through the window 210 occurs when each axis of the pair falls on a common elevation of the inclined window. Referring now to FIG. 4, to enable the viewing axes 260 and 270 to fall on a common elevation of the inclined window 210, the view portal 170 is mounted on the objective lens barrel 60 to have a rotational orientation to the lens barrel which ensures that the viewing axes intersect a plane defined by the inclined window 210 to establish an intersection axis 300 substantially normal to an imaginary line intersecting the frame central axis 190 and perpendicular to the central axis 190 itself. Thus, optimum viewability through the window 210 of the view portal 170 is ensured if the acute inclination of the window defined by the intersection axis 300 is directed towards the first ocular port 40 of the microscope of FIG. 1, or away from the first ocular port and towards the second ocular port 50, which is preferably located 180 degrees from the first ocular port. Such a rotational orientation also has the advantage of providing a constant laser divergence that can be programmed into the computer during image guided procedures.

For a view portal 170 utilizing at least one tab 204 on its frame outer surface 200 for engagement with the recess 66 of the objective lens barrel inner peripheral wall 62, the direction of acute inclination of the window 210 can be rotationally oriented with the at least one tab, and the recess similarly rotationally oriented within the lens barrel, to ensure that the direction of inclination is towards either the first or second ocular ports 40 or 40 when the tab of the frame engages the recess of the barrel. For a view portal 170 utilizing at least one raised resilient surface 202 on its frame outer surface 200 for engagement with the objective lens barrel inner peripheral wall 62, the direction of acute inclination of the window 210 can be indicated by a locator 250 rotationally oriented with and attached to the cylindrical frame 180 of the view portal 170. In the embodiment of the invention illustrated in FIG. 3, the locator is preferably comprised of a button 252 located on a first of two grips 254 and 256 extending downwardly from the second end 184 of the frame 180. The two grips 254 and 256 provide a gripping surface of the view portal 170 for the surgeon to hold when mounting the portal on the objective lens barrel. The button 252 indicates to the surgeon that the view portal 170 should be mounted on the lens barrel 60 with the button 252 facing preferably either the first or second ocular port 40 or 50 of the microscope 10, depending on the type of operation performed. Although button 252 is used as the locator 250 in the preferred embodiment of the drape assembly 70, it is understood that other visual or tactile indications (i.e. a line) may be utilized to indicate the preferred rotational orientation as well.

It is noted that the addition of a fourth ocular pocket to the drape assembly 70 (i.e. the addition of ocular pocket 140) is beneficial to the rotational orientation of the view portal 170 to the objective lens barrel 60. After mounting the view portal 170 on the objective lens barrel 60 with a rotational orientation to establish optimum viewability through the portal, the fourth ocular pocket 140 of the drape is available for placement over second ocular port 50, located preferably opposite from the first ocular port 40 during spinal operations, without requiring the view portal to be removed from the barrel to allow a rotation of the hollow enclosure 80 to accommodate the second ocular port. Such a procedure is routinely required with prior art drapes having less than 4 ocular pockets, with the disconnection of the view portal 170 from the objective lens barrel 60 having the undesirable side effect of compromising the optimal viewability of the view received by the objective lens.

Returning to a discussion of the components of the view portal 170, a flange 310 is located proximal to the second end 184 of the cylindrical frame 180, extending outwardly from the frame's outer surface 200. As shown in FIGS. 3 and 4, the flange 310 is adapted for attachment to the sheet-form material of the drape assembly 70 about the hole 120 of the enclosure 80 to form a hermetically sealed connection between the two. The sheet-form material may be attached to the flange via adhesives, heat bonding, or other similar methods understood in the art. While the sheet-form material is shown in FIGS. 3 and 4 as being attached to a surface of the flange 310 facing the window 210, it is understood that the material can be attached to the opposite surface of the flange, as well as the outer peripheral surface thereof. Thus, with the sheet form material attached to the flange 310 of the cylindrical frame 180, the frame and window of the view portal 170 seals the hole 120 in the enclosure 80.

In use, the access opening of the first end of the hollow enclosure of the drape assembly is pulled over a given surgical microscope so that the access opening is located away from the microscope's head. The second end of the hollow enclosure of the drape assembly is pulled over the head of the microscope, with the view portal of the drape assembly located on a lower surface of the enclosure proximal to the microscope's objective lens barrel. The grips of the view portal are held as the first end of the cylindrical frame and window of the portal is inserted inside the cavity of the lens barrel. If the view portal includes at least one tab on the outer surface of the frame, the at least one tab is inserted into an at least one recess opening located at the bottom of the inner peripheral wall of the lens barrel and the frame and the frame is raised and rotated until the at least one tab is seated in the least one recess of the lens barrel inner peripheral wall.

The engagement of the tab and recess ensures that the view portal is properly rotationally oriented to the lens barrel with the acute inclination of the window facing either the first or second view ports of the microscope. If the view portal utilizes a raised resilient surface on the frame outer surface to engage the inner peripheral wall of the barrel, the view portal is rotated on the barrel to ensure that the button locator of the first grip is directed towards the first or second view ports. After the view portal is mounted on the barrel and the rotational orientation between the two is established, the hollow enclosure is positioned about the microscope so that the ocular pockets of the enclosure cover the corresponding ocular ports of the microscope. When the surgical procedure has concluded, the view portal is removed from the objective lens barrel and the enclosure and ocular pockets are pulled from the head of the microscope until the passageway located at the first end of enclosure is pulled over the microscope's head, thus removing the drape assembly from the microscope.

What is claimed is:

1. A drape assembly for maintaining a sterile field around a surgical microscope having at least one ocular port defining a pair of viewing axes, an illumination source defining an illumination axis, and an objective lens barrel having an inner peripheral wall defining a cavity, the assembly comprising:

an elongated hollow enclosure of sheet-form material having a first end defining an access opening and a second end defining a hole;

a cylindrical frame defining a central axis and located on the enclosure second end, the cylindrical frame having an outer surface engageable with the inner peripheral wall of the objective lens barrel for mounting the frame on the barrel, the frame including a window support adapted to be located within the cavity when the outer surface engages the inner peripheral wall; and a window located on the window support such that the window intersects the viewing axes when the frame is mounted on the barrel, the frame and window sealing the hole in the enclosure.

2. The drape assembly of claim 1 wherein the engageable outer surface of the cylindrical frame includes at least one raised resilient surface engageable with the inner peripheral wall of the objective lens barrel.

3. The drape assembly of claim 1 wherein the engageable outer surface of the cylindrical frame includes at least one tab engageable with at least one recess located within the inner peripheral wall of the objective lens barrel.

4. The drape assembly of claim 1 wherein the window defines a plane acutely inclined from the central axis of the frame, the window having an upper surface receiving the illumination axis from the illumination source.

5. The drape assembly of claim 4 further including a locator on the frame rotationally oriented in relation to the objective lens barrel to define an intersection axis substantially normal to the viewing axes at the intersection of the viewing axes and the plane.

6. The drape assembly of claim 5 wherein the rotational orientation directs the acute inclination of the window towards the at least one ocular port.

7. The drape assembly of claim 5 wherein the rotational orientation directs the acute inclination of the window away from the at least one ocular port.

8. The drape assembly of claim 4 wherein the acute inclination defines an angle from the central axis of from about 81 degrees to about 83 degrees.

9. A drape assembly for enclosing at least a portion of a surgical microscope having at least one ocular port defining a pair of viewing axes, an illumination source defining an illumination axis, and an objective lens barrel having an inner peripheral wall defining a cavity, the assembly comprising:

an elongated hollow enclosure of sheet-form material having a first end defining an access opening and a second end defining a hole;

a cylindrical frame defining a central axis and located on the enclosure proximal to the second end, the cylindrical frame having an outer surface engageable with the inner peripheral wall of the objective lens barrel for mounting the frame on the barrel, the frame including a window support adapted to be located within the cavity when the outer surface engages the inner peripheral wall; and a window located on the window support such that the window intersects the viewing axes when the frame is mounted on the barrel, the window defining a plane acutely inclined from the central axis from about 81 degrees to about 83 degrees with the window having an upper surface receiving the illumination axis from the illumination source, the frame and window sealing the hole in the enclosure.

10. The drape assembly of claim 9 further including a locator on the frame rotationally oriented in relation to the objective lens barrel to define an intersection axis substantially normal to the viewing axes at the intersection of the viewing axes and the plane.

11. The drape assembly of claim 10 wherein the rotational orientation directs the acute inclination of the window towards the at least one ocular port.

12. The drape assembly of claim 10 wherein the rotational orientation directs the acute inclination of the window away from the at least one ocular port.

13. The drape assembly of claim 9 wherein the engageable outer surface of the cylindrical frame includes at least one raised resilient surface engageable with the inner peripheral wall of the objective lens barrel.

14. The drape assembly of claim 9 wherein the engageable outer surface of the cylindrical frame includes at least one tab engageable with at least one recess located within the inner peripheral wall of the objective lens barrel.

15. A drape assembly for enclosing at least a portion of a surgical microscope having at least one ocular port defining a pair of viewing axes and an illumination source defining an illumination axis, the surgical microscope having an objective lens barrel with an inner peripheral wall defining a cavity, the assembly comprising:

an elongated hollow enclosure of sheet-form material having a first end defining an access opening and a second end defining a hole;

a cylindrical frame defining a central axis and located on the enclosure proximal to the second end, the cylindrical frame having an outer surface engageable with the inner peripheral wall of the objective lens barrel for mounting the frame on the barrel, the frame including a window support adapted to be located within the cavity when the outer surface engages the inner peripheral wall; and a window located within the cylindrical frame and intersecting the viewing axes and illumination axis when the frame is mounted on the barrel, the window defining a plane acutely inclined from the illumination axis with the window having an upper surface receiving the illumination axis from the illumination source, the frame and window sealing the hole in the enclosure.

16. The drape assembly of claim 15 wherein the acute inclination defines an angle from the illumination axis of from about 77 degrees to about 81 degrees.

17. The drape assembly of claim 15 further including a locator on the frame rotationally oriented in relation to the objective lens barrel to define an intersection axis substantially normal to the viewing axes at the intersection of the viewing axes and the plane.

18. The drape assembly of claim 17 wherein the rotational orientation directs the acute inclination of the window towards the at least one ocular port.

19. The drape assembly of claim 17 wherein the rotational orientation directs the acute inclination of the window away from the at least one ocular port.

20. The drape assembly of claim 15 wherein the engageable outer surface of the cylindrical frame includes at raised resilient surface engageable with the inner peripheral wall of the objective lens barrel.

21. The drape assembly of claim 15 wherein the engageable outer surface of the cylindrical frame includes at least tab engageable with at least one recess located within the inner peripheral wall of the objective lens barrel.

22. A drape assembly for enclosing at least a portion of a surgical microscope having at least 4 ocular ports, the ports each defining a pair of viewing axes and the surgical microscope having an objective lens barrel with an inner peripheral wall defining a cavity, the assembly comprising:

an envelope of sheet-form material having opposite ends, one end of the envelope defining an access opening and the other end of the envelope defining a hole and at least 4 ocular pockets;

a cylindrical frame defining a central axis and located on the envelope proximal to said other end, the cylindrical frame engageable with the objective lens barrel for mounting the frame on the barrel, the frame including a window support; and a window located on the window support such that the window intersects the viewing axes when the frame is mounted on the barrel, the frame and window sealing the hole in the enclosure and the window defining a plane acutely inclined from the central axis, the frame having a locator rotationally oriented in relation to the objective lens barrel to define an intersection axis substantially normal to the viewing axes at the intersection of the viewing axes and the plane.

23. The drape assembly of claim 22 wherein the rotationally orientation directs the acute inclination of the window towards a first ocular port of the at least 4 ports.

24. The drape assembly of claim 22 wherein the rotational orientation directs the acute inclination of the window away from a first ocular port of the at least 4 ports.

25. The drape assembly of claim 22 wherein the acute inclination defines an angle from the central axis of from about 81 degrees to about 83 degrees.

26. The drape assembly of claim 22 wherein the frame has an outer surface engageable with the inner peripheral wall of the objective lens barrel and the window support is adapted to be located within the cavity where the outer surface engages the inner peripheral wall.

27. The drape assembly of claim 26 wherein the engageable outer surface of the cylindrical frame includes at least one raised resilient surface engageable with the inner peripheral wall of the objective lens barrel.

28. The drape assembly of claim 26 wherein the engageable outer surface of the cylindrical frame includes at least one tab engageable with at least one recess located within the inner peripheral wall of the objective lens barrel.

29. A view portal for a surgical microscope drape for maintaining a sterile field around a surgical microscope, the drape defining an elongated hollow enclosure of sheet-form material having an access opening located at one end and a hole located proximal to an opposite end, the microscope having at least one ocular port defining a pair of viewing axes and an objective lens barrel having an inner peripheral wall defining a cavity, the portal comprising:

a cylindrical frame defining first and second ends and a central axis, the frame having an outer surface engageable with the inner peripheral wall of the objective lens barrel for mounting the frame on the barrel;

a window support located proximal to the first end of the cylindrical frame and adapted to be located within the cavity of the objective lens barrel when the outer surface engages the inner peripheral wall;

a flange located proximal to the second end of the of the cylindrical frame and extending outwardly of the frame's outer surface, the flange adapted for attachment to the sheet-form material of the drape about the hole; and a window located on the window support such that the window is located within the cavity of the barrel and intersects the viewing axes of the microscope when the frame is mounted on the barrel.

30. The view portal of claim 29 wherein the engageable outer surface of the cylindrical frame includes at least one raised resilient surface engageable with the inner peripheral wall of the objective lens barrel.

31. The view portal of claim 29 wherein the engageable outer surface of the cylindrical frame includes at least one tab engageable with at least one recess located within the inner peripheral wall of the objective lens barrel.

32. The view portal of claim 29 wherein the window defines a plane acutely inclined from the central axis of the frame.

33. The view portal of claim 32 further including a locator on the frame rotationally oriented in relation to the objective lens barrel, when mounted thereon, to define an intersection axis substantially normal to the viewing axes at the intersection of the viewing axes and the plane.

34. The view portal of claim 33 wherein the rotational orientation directs the acute inclination of the window towards the at least one ocular port.

35. The view portal of claim 33 wherein the rotational orientation directs the acute inclination of the window away from the at least one ocular port.

36. The view portal of claim 32 wherein the acute inclination defines an angle from the central axis of from about 81 degrees to about 83 degrees.

* * * * *

UNITED STATES PATENT AND TRADEMARK OFFICE
CERTIFICATE OF CORRECTION

PATENT NO.    : 6,902,278 B2                                              Page 1 of 1
DATED         : June 7, 2005
INVENTOR(S)   : Bala It is certified that error appears in the above-identified patent and that said Letters Patent is hereby corrected as shown below:

Column 9,
Line 28, the text reading "the angle a" should be changed to -- the angle $\alpha$ --.

Signed and Sealed this

Twenty-ninth Day of November, 2005

JON W. DUDAS
*Director of the United States Patent and Trademark Office*